Figure 1:
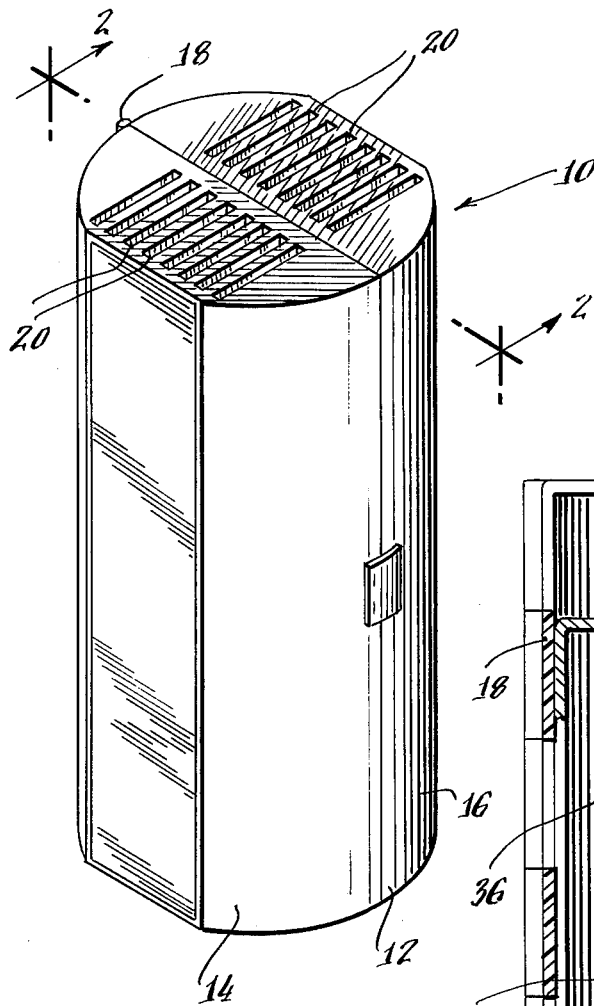
Figure 2:
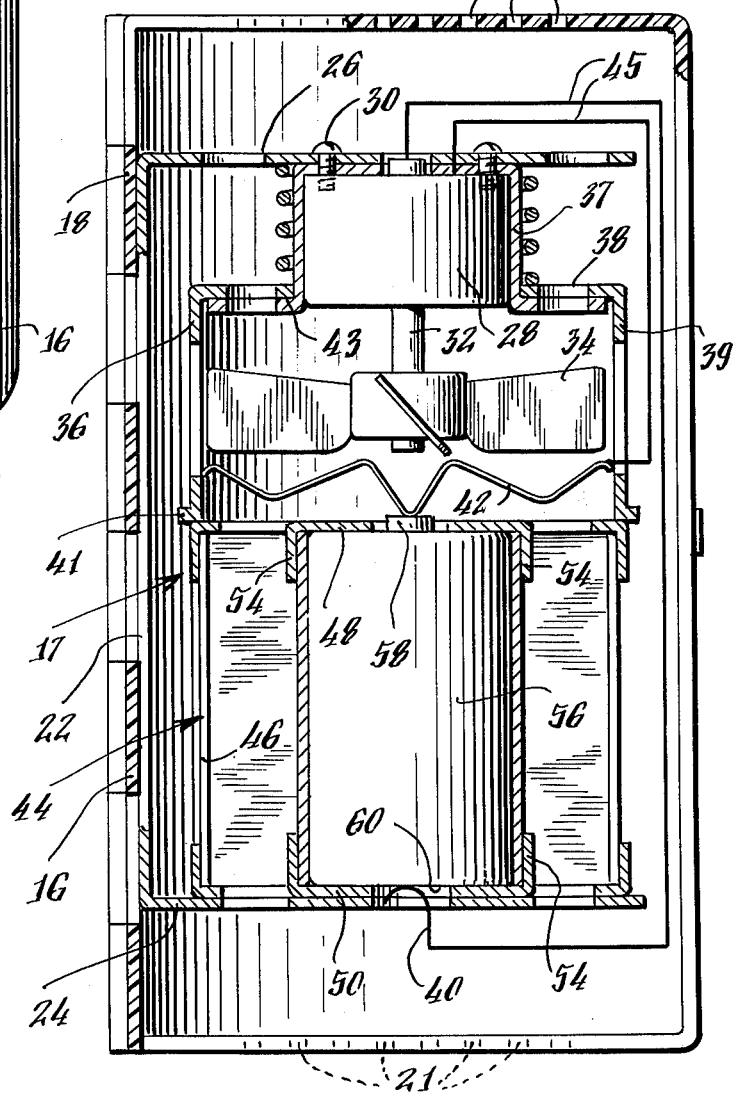
Figure 3:
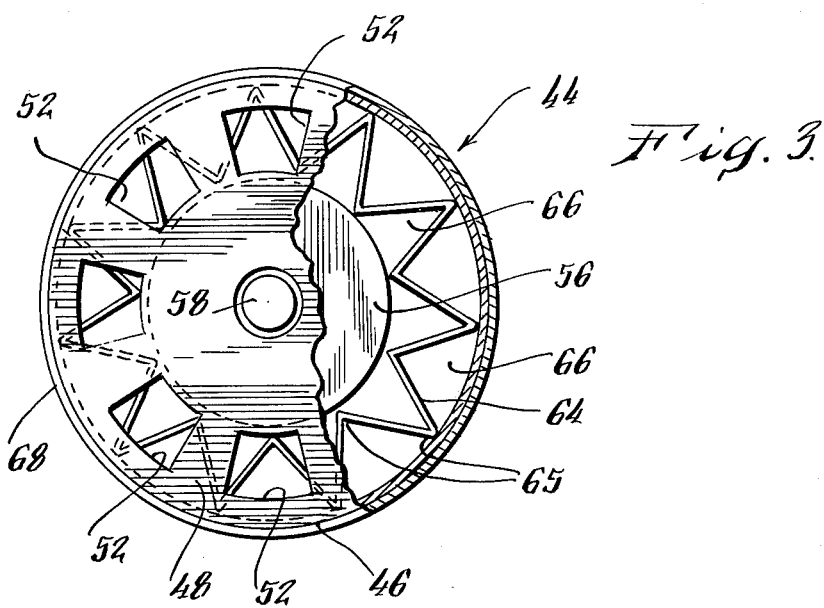

United States Patent

Tringali

[11] 4,035,451
[45] July 12, 1977

[54] CARTRIDGE FORMING PART OF A SYSTEM FOR INDUCING AIR FLOW PAST A PRODUCT CAPABLE OF BEING VAPORIZED

[75] Inventor: Dominick Tringali, Columbia, S.C.

[73] Assignee: The Risdon Manufacturing Company, Naugatuck, Conn.

[21] Appl. No.: 707,954

[22] Filed: July 23, 1976

[51] Int. Cl.² .......................................... A61L 9/00
[52] U.S. Cl. ........................ 261/101; 21/53; 21/74 R; 21/109; 21/126; 261/30
[58] Field of Search ............ 261/30, 101, 95; 21/109, 126, 74 R, 53

[56] References Cited

U.S. PATENT DOCUMENTS

| 3,804,592 | 4/1974 | Garbe | 21/53 |
| 3,846,404 | 11/1974 | Nichols | 106/196 |
| 3,955,922 | 5/1976 | Moulthrop | 21/74 R |
| 3,990,848 | 11/1976 | Corris | 21/74 R |
| 3,993,444 | 11/1976 | Brown | 21/74 R |

Primary Examiner—Tim R. Miles
Assistant Examiner—Gregory N. Clements
Attorney, Agent, or Firm—St. Onge, Mayers, Steward & Reens

[57] ABSTRACT

A cartridge, which forms part of a system for inducing air flow past a product capable of being vaporized, includes a hollow, apertured container and a support of strip material having a convoluted configuration mounted in the container. A quantity of the product is impregnated in the support of strip material. The container also houses a battery which has exposed terminals. The cartridge of the invention is used with an apparatus that has a housing defining a cartridge receiving cavity shaped and dimensioned to receive the cartridge container, a fan mounted in the housing to induce air flow through the cavity, and electrically powered motor for driving the fan and contacts electrically connected to the motor and located to contact the battery terminals when the cartridge is received in the cavity.

7 Claims, 4 Drawing Figures

CARTRIDGE FORMING PART OF A SYSTEM FOR INDUCING AIR FLOW PAST A PRODUCT CAPABLE OF BEING VAPORIZED

BACKGROUND OF THE INVENTION

1. Field of the Invention

The present invention relates to a system, and particularly, to a cartridge which forms part of the system, for inducing air flow past a product which may be vaporized in order to aid distribution of the product into the environment.

Many products which are desirably distributed in their environment such as room deodorizers, insecticides, germicides and the like are now manufactured in solid form, for example, as a gel. Such products in solid or liquid form have also been impregnated in porous materials. In both cases, the products are released into the environment in which they are exposed by a vaporization process such as evaporation or sublimation.

Though most products of the type described above are now used merely by mounting and exposing them in the environment to be treated, it is preferable in certain applications to induce greater distribution of the product than is possible by this technique.

2. Description of the Prior Art

Systems for inducing air currents past products which can be vaporized as a means of assuring greater and more even product distribution are known. For example, U.S. patent application Ser. No. 566,960 (Corris), assigned to the assignee of the present invention, discloses a system having an apparatus which includes a housing, that defines a cartridge receiving chamber, and a fan and a motor for driving the fan mounted in the housing. A cartridge including a mass of product capable of being vaporized and a battery, both mounted with a container, is adapted to be inserted in the cartridge receiving chamber of the housing. The motor is powered by the cartridge battery to drive the fan and thus induce air flow through the cartridge container past the mass of product and out of the apparatus housing.

The configuration of the cartridge used in the Corris system has certain drawbacks. Since the product is in concentrated single mass, usually in gel form, a relatively small surface area of product as a function of its mass is presented to air flow. The cartridge of the present invention is an improvement on the Corris design.

Other systems are also known. For example, U.S. Pat. No. 3,522,935 (Lewis) discloses an air treatment device which has an oscillating vane that effects a steady current of air over a wick which projects out of the container of liquid deodorant. The vane is propelled by an electromagnet which is periodically energized to repell a permanent magnet linked to the vane.

U.S. Pat. No. 2,614,820 (Boydjieff) discloses an air perfuming device which includes a motor-driven fan, powered by alternating current, that induces air flow over a sponge which soaks up a perfuming liquid.

U.S. Pat. Nos. 2,629,149 (Yaffe) and 2,510,126 (Melcher et al.) respectively disclose deodorizing and demothing devices which have motor driven fans, powered by alternating current, for effecting air flow over appropriate products.

However, none of the devices disclosed in the patents mentioned above includes a cartridge which both houses a product that may be vaporized and a source of power for an apparatus that induces air flow past the product. Each includes a power supply and a product container which are mutually independent. Therefore, each has several drawbacks.

Porous materials, which may be impregnated with products that can be vaporized or which carry such products in other ways are also known. For example, U.S. Pat. No. 3,846,404 (Nichols) dicloses a process of preparing ultramicroporous gelled cellulose triacetate products which can be used as carriers for liquids such as perfumes to make the liquids available for extended periods of time. U.S. Pat. No. 3,926,655 (Miles) discloses a clear polyamide resin material which contains a perfume oil.

SUMMARY OF THE INVENTION

In a preferred embodiment, to be described below in detail, the cartridge of the present invention is self-contained, replaceable and disposable. It houses both a product to be vaporized and a source of power for an apparatus which induces air flow past the product. The manner in which the product is mounted in this cartridge permits overall size of the cartridge to be greatly reduced while nevertheless exposing a large product surface area to the air flow. Therefore, it may be more efficiently packaged and distributed.

The cartridge of the invention was designed as a part of a system that includes an apparatus for inducing air flow past the product which is capable of being vaporized. This apparatus includes a housing which defines a cartrige receiving cavity. A fan is mounted in the housing to induce air flow through the cartridge receiving cavity and out of the housing and is driven by a motor also mounted in the housing. Contacts are electrically connected to the motor and are located in the cartridge receiving cavity.

The self-contained, replaceable and disposable cartridge of the present invention comprises a hollow, apertured container which is shaped and dimensions to be received in the cartridge receiving cavity of the apparatus housing. A battery is mounted in the container and is equipped with exposed terminals. These terminals are located to make electrical contact with the apparatus contacts electrically connected to the motor which drives the fan.

The container has a larger inside cross-sectional area than the outside cross-sectional area of the battery. Therefore, a space is defined between them. A support of strip material is mounted in this space and has a convoluted configuration having folds whih extend in the direction of the major container-battery dimension. A quantity of the product, which may be, for example, a deodorizer, germicide, or insecticide and which is capable of being vaporized, is impregnated in or otherwise carried by the support of strip material to be released in vapor form when air flow is induced thereby. The strip material may be of the type described in U.S. Pat. No. 3,846,404 (Nichols) impregnated with an appropriate product.

The container is apertured at its top and bottom so that the adjacent convolutions of the strip of support material define air passageways which extend in the direction of the major container-battery dimension. Accordingly, when the cartridge is inserted into the apparatus housing cartridge receiving cavity, and the battery terminals are connected to the contacts located therein, the fan is driven by the motor to induce air flow through these passages in order to vaporize the product impregnated in the strip material support and distribute it in the environment of the apparatus.

The system of which the cartridge of the present invention forms a part, provides several advantages. It is completely portable since it is battery powered. It may be used indoors or out at any time without regard to the availability of alternating current. The cartridge arrangement provides a convenient means for handling and distributing both the battery and the product. Particularly, when the product is exhausted, a new cartridge is merely inserted into the apparatus to simultaneously provide a fresh supply of power for the battery driven motor as well as a fresh supply of product.

Accordingly, it is an object of the present invention to provide a cartridge, housing both a product which is capable of being vaporized to be distributed into its environment as well as a source of power for an apparatus that induces air flow past the product. Other objects, aspects, and advantages of the present invention will be pointed out in, or will be understood from, the following detailed description provided below in conjunction with the accompanying drawings.

BRIEF DESCRIPTION OF THE DRAWINGS

FIG. 1 is a perspective view of the system of the present invention for inducing air flow past a product which is capable of being vaporized.

FIG. 2 is a vertical cross-sectional view taken through plane 2—2 in FIG. 1 illustrating the cartridge of the present invention installed in the apparatus for inducing air flow past the product contained in it.

FIG. 3 is a top plan view of the cartridge.

FIG. 4 is a perspective view of the cartridge shown with temporary end caps, one of which is installed and the other of which is removed.

DETAILED DESCRIPTION OF THE PREFERRED EMBODIMENT

FIG. 1 illustrates the system, of which the cartridge of the present invention forms a part, that includes an apparatus for inducing air flow past a product which may be vaporized. The apparatus, generally indicated at 10, includes a generally cylindrical housing 12 made of molded plastic or other suitable material and has front and rear sections 14 and 16 joined in clam shell fashion by a hinge 18 which permits one section to be opened from the other. When closed, the housing sections define a cartridge receiving cavity 17 shaped and dimensioned to receive a cartridge in a manner described below. Both the top and bottom of each housing section are formed with open grills 20 and 21 which permit air flow to be induced through the housing. The rear section is preferably mounted on a wall or other upright structure so that these grills are fully exposed in the environment.

As shown in FIG.d 2, a frame 22 is mounted inside the rear section 16 of housing 12 and includes an apertured lower plate 24 and a similarly apertured upper plate 26. A small direct current powered motor 28 is mounted by any suitable means such as screws 30 to the frame upper plate 26. A rotatably shaft 32 depends from motor 28 and a fan 34 is attached for rotation thereto.

A depending cyclindrical shroud 36 is also mounted on upper fram plate 26. A small diameter portion 37 of this shroud 36 encloses motor 28 and a larger diameter portion 39 loosely envelops the edges of the blades of fan 34. A small radially outwardly directed flange 41 is formed at the bottom margin of the larger diameter portion 39 is spaced from the lower plate 24 of frame 22. A radially outwardly directed web 43 which interconnects the small and large diameter shroud portions is apertured at 38 to permit free flow of air axially through the housing 12.

A pair of electrical contacts 40 and 42 are also mounted with the frame 26. The lower contact 40 is mounted in the center of lower frame plate 24 and an upper contact 42 is mounted in the center of and spans shroud 36. Both contacts are electrically connected to motor 28 by leads 45 which extend through the housing section 16.

The cartridge of the present invention which cooperates with the apparatus explained in detail above may be described with reference to FIGS. 2 through 4. This cartridge, generally indicated at 44, includes a cylindrical housing 46 which may be made of any suitable imperforate material such as pressed paper, injection molded plastic, or sheet metal. The housing is completed by an apertured top 48 and bottom 50 made of rigid material such as plastic or metal. In the preferred embodiment, both the top and bottom are punched or otherwise formed with apertures 52, shown in FIG. 3, and with inwardly projecting tabs 54.

A cylindrical battery 56 is mounted in the cylindrical container 46 and is held in coaxial relation therewith by the tabs 54. As can be seen in FIG. 2, the battery has a positive terminal 58 exposed through the container top 48 and a negative terminal 60 exposed through the container bottom 50. When the cartridge 44 is mounted in the cartridge receiving chamber 17 the negative terminal of battery 56 makes electrical contact with lower contact 40 and the positive terminal makes electrical contact with upper contact 42. In this manner, the motor 28 receives electrical power to drive fan 34.

An annular space 62 is defined between the cylindrical container 46 and the side of battery 56. A support of strip material 64 is mounted with a convoluted configuration in this annular space. In the preferred embodiment, the convolutions take the form of an accordian pleat having folds 64 which extend parallel to the common axis of battery 56 and container 46 to thus define a series of parallel air passageways 66. Of course, other convoluted configurations may be devised for mounting the support of strip material in the container with the battery. However, it is important that a large amount of surface area of the strip material be presented to insure proper distribution of the product impregnated or carried by it.

It has been found that strip material such as that disclosed in U.S. Pat. No. 3,846,404 (Nichols) makes a suitable support. However, any other type of material which will hold or carry a product capable of being vaporized and which will permit the product to be released in a controlled prolonge manner may be used.

As can be seen in FIG. 2, the cartridge container 46, enclosed by its top 48 and bottom 50, is shaped and dimensioned to be snugly, yet removably received between frame lower plate 24 and shroud flange 41. Accordingly, a closed air flow path is defined through bottom grill 21, the apertured lower frame plate 24, the cartridge flow paths, shroud apertures 38, the apertured upper frame plate 26 and top grill 20. Moreover, when the cartridge container is snugly inserted between plate 24 and flanges 41, lower electrical contact 40 touches the negative battery terminal and upper contact 42 touches the positive battery terminal in order to power motor 28 and drive fan 34. Of course, the fan may be driven in either a clockwise or counter-clockwise direction to induce air flow in an upward or downward direction through the cartridge. Moreover, the fan may, as conveniently, be mounted below the cartridge in the housing.

The apparatus 10 may incorporate a timing network for automatically and periodically, instead of continuously, powering the motor. In this way, motor life is increased. A suitable timing network is disclosed in U.S. Pat. No. 3,739,944 (Rogerson).

Figure 4:
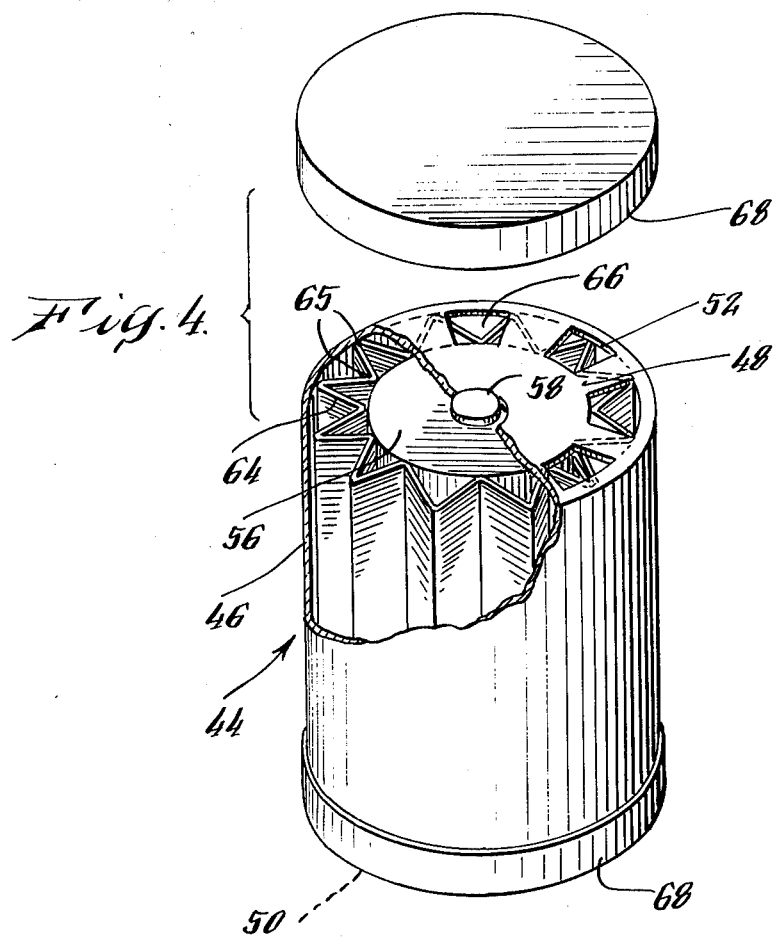

FIG. 4 illustrates the cartridge of the present invention assembled for shelf storage and distribution. As shown there, the cartridge has a protective cover 68 on both its top and bottom which may be made of paper plastic and which are removed by the user prior to the insertion into the apparatus for inducing air flow through it.

The cartridge 44 of the invention is disposable, self-contained and replaceable. That is, when the product impregnated or carried in the strip material has been exhausted through vaporization, the entire cartridge is removed from the apparatus and is discarded. A new cartridge is then merely inserted into the apparatus for repeated use. It is desirable that the battery and product impregnated strip material be designed so that each is exhausted at approximately the same time for optimal efficiency of use.

Although a preferred embodiment of the present invention has been described above in detail, it is to be understood that this is for purposes of illustration. Modifications may be made to the described structure by those skilled in the art in order to adapt this cartridge for housing both a source of power and a product capable of being vaporized for use in an apparatus for inducing air flow past the product to particular applications.

What is claimed is:

1. In a system including an apparatus for inducing air flow past a product capable of being vaporized to release the product in vapor form into the environment, the apparatus including a housing defining a cartridge receiving cavity, fan means mounted in the housing to induce air flow through the cartridge receiving cavity and out of the housing, elecrically powered motor means for driving the fan means, and contact means electrically connected to the motor means mounted in the housing for contacting and electrically connecting a supply of electrical power to the motor means; a self-contained replaceable and disposable cartridge adapted to cooperate with the apparatus, said cartridge comprising:
   A. a hollow apertured container shaped and sized to be received in the cartridge receiving cavity;
   B. a support of strip material, mounted in said container, having a convoluted configuration;
   C. a quantity of a product, which is capable of being vaporized, carried by said support of strip material; and
   D. a battery mounted in said container and equipped with terminals which are exposed by the container and are located to make electrical contact with the contact means when said container is received in the cartridge receiving cavity whereby, when so received, said battery powers the motor means to drive the fan means and induce air flow past said support and, thus, said product.

2. The self-contained replaceable and disposable cartridge adapted to cooperate with an apparatus for inducing air flow past a product which is capable of being vaporized as claimed in claim 1, wherein said battery has cross-sectional area less than the interior cross-sectional area of said container, said battery being mounted in said container to define a space therebetween extending in the direction of the major container-battery dimension, said battery terminals being exposed respectively at the top and bottom of said container.

3. The self-contained replaceable and disposable cartridge adapted to cooperate with an apparatus for inducing air flow past a product which is capable of being vaporized as claimed in claim 2 wherein said support of strip material is mounted in said space and is pleated, having folds which extend in the direction of the major container-battery dimension to define a plurality of air passageways.

4. The self-contained replaceable and disposable cartridge adapted to cooperate with an apparatus for inducing air flow past a product which is capable of being vaporized as claimed in claim 3 wherein said container is apertured at its top and bottom at opposite ends of said plurality of air passageways.

5. The self-contained replaceable and disposable cartridge adapted to cooperate with an apparatus for inducing air flow past a product which is capable of being vaporized as claimed in claim 4 wherein the side wall of said container is substantially imperforate in order to channel all air flow therethrough through said plurality of passageways.

6. The self-contained replaceable and disposable cartridge adapted to cooperate with an apparatus for inducing air flow past a product which is capable of being vaporized as claimed in claim 1 wherein said battery and product have approximately the same useful life and are therefore exhausted by operation of the apparatus at approximately the same time.

7. In a system including an apparatus for inducing air flow past a product capable of being vaporized to release the product in vapor form into the environment, the apparatus including a frame, electrically powered motor means mounted in the frame, fan means driven by the motor means and contact means electrically connected to the motor means mounted in the frame; a self-contained, disposable, and replaceable cartridge adapted to cooperate with the apparatus, said cartridge comprising:
   A. an apertured container formed to be mounted on the frame in operative relation to the fan means;
   B. a battery mounted in said container, having terminals exposed thereby and located to make electrical connection with the contact means when said container is mounted on the frame; and
   C. a product support of strip material, having a quantity of product capable of being vaporized therein, formed in a convoluted shape to define air flow passages through said container which extend in the direction of air flow induced by the fan.

* * * * *